(12) United States Patent
Wrobel et al.

(10) Patent No.: US 6,200,963 B1
(45) Date of Patent: Mar. 13, 2001

(54) ARYL SULFONIC ACIDS AS FSH ANTAGONISTS

(75) Inventors: Jay E. Wrobel, Lawrenceville, NJ (US); John F. Rogers, Bryn Mawr; Wenling Kao, Chester, both of PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/537,472

(22) Filed: Mar. 24, 2000

Related U.S. Application Data

(60) Provisional application No. 60/155,220, filed on Mar. 31, 1999.

(51) Int. Cl.[7] ............... A61K 31/655; C07C 309/35; C07D 251/22
(52) U.S. Cl. ............... 514/150; 534/872; 534/638
(58) Field of Search ............... 534/638, 872; 514/150

(56) References Cited

U.S. PATENT DOCUMENTS

| | | | |
|---|---|---|---|
| 724,078 | * 3/1903 | Bertschmann | 534/827 |
| 2,102,115 | * 12/1937 | Fleischhauer et al. | 534/872 |
| 5,300,633 | 4/1994 | Dannheim et al. | |
| 5,484,458 | 1/1996 | Russ et al. | |
| 5,539,088 | 7/1996 | Schumacher et al. | |
| 6,025,478 | 2/2000 | Kunde et al. | |

FOREIGN PATENT DOCUMENTS

| | | |
|---|---|---|
| 0463656 | 10/1968 | (CH). |
| 0272532 | 5/1991 | (EP). |
| 0624630 | 11/1994 | (EP). |
| 0630946 | 12/1994 | (EP). |
| 1517223 | 2/1968 | (FR). |
| 9307864 | 4/1993 | (WO). |

OTHER PUBLICATIONS

Sekido et al., Chemical Abstracts, 53:15569h, 1959.*
Fisichella et al., Chemical Abstracts, 95:134353, 1981, Registry No. 78866–14–5.*
Chemical Abstracts, Registry Handbook, 1978, Part 2, p. 2119RG, Registry No 67990–25–4.*
Rivlin, Introduction to the Dyeing of Textile Fibers, Philadelphia College of Textiles and Science, Philadelphia, PA, 1982, p. 37.*
Colour Index, 3rd Edition, 1971, vol. 4, p. 4111, C.I. 17820.*
Daugherty et al., J. Urol., 1992, 147, 727–732.
Danesi et al., J. Clin. Endocrinol. Metab., 1996, 81, 2238–2246.
Ruggli et al., Helv. Chim. Acta., 1939, 22, 1170–1177.
Szadowski et al., Barwniki, Srodki Pomocnicze, 1996, 40, 55–62.

* cited by examiner

Primary Examiner—Fiona T. Powers
(74) Attorney, Agent, or Firm—Steven R. Eck

(57) ABSTRACT

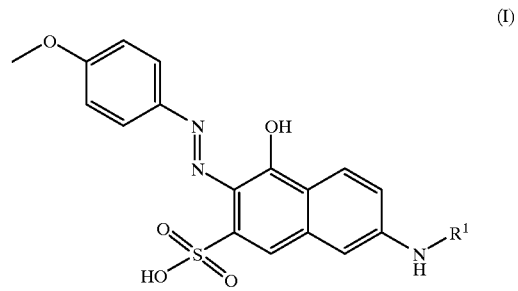

wherein:

$R^1$ is a moiety selected from:

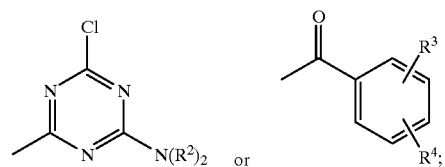

$R^2$ is $CH_2CH_2CONH_2$ or $CH_2CH_2OH$;
$R^3$ and $R^4$ are independent substituents selected from the group including H, $-N(CH_3)_2$, or $-OCH_3$;
or pharmaceutically acceptable salts thereof.

18 Claims, No Drawings

ARYL SULFONIC ACIDS AS FSH ANTAGONISTS

This application claims the benefit of U.S. Provisional Application No. 60/155,220, which was converted from U.S. patent application Ser. No. 09/282,827, filed Mar. 31, 1999, pursuant to a petition filed under 37 C.F.R. 1.53(c)(2)(i).

This invention relates to novel aryl sulfonic acids which function as FSH antagonists. More particularly, the compounds of this invention antagonize the binding of hFSH to its receptor and block cellular functions of FSH, including the production of second messenger cAMP and estradiol in ovarian and granulosa cells and are useful as female and male contraceptive agents.

BACKGROUND OF THE INVENTION

Reproduction in women depends upon the dynamic interaction of several compartments of the female reproductive system. The hypothalamic-pituitary unit orchestrates a series of events affecting the ovaries and the uterine-endometrial compartment which leads to the production of the ovum, ovulation, and ultimately appropriate conditions for fertilization. Specifically, hypothalamic hormones enhance the release of the gonadotropins luteinizing hormone (LH) and follicle stimulating hormone (FSH). In the ovary, gonadotropins enhance the development of follicles which, in turn, secrete steroids (estradiol, progesterone) and peptides (inhibin, activin). Estradiol and inhibin levels progressively increase during the follicular phase of the menstrual cycle until ovulation. Afterwards, the follicular unit forms the corpus luteum which produces progesterone. Ovarian hormones, in turn, regulate the secretion of gonadotropins by establishing a classical long-loop negative feedback mechanism. The elucidation of these control mechanisms has provided opportunities for the development of effective strategies to control fertility, including both the enhancement of fertility and contraception. For recent reviews of FSH action see "FSH Action and Intraovarian Regulation", B. C. J. M. Fauser, editor, Parthenon Publishing Group, 1997 and Hsueh, A. J., Bicsak, T., Jia, X. -C., Dahl, K. D., Fauser, B. C. J. M., Galway, A. B., Czwkala, N., Pavlou, S., Pakoff, H., Keene, J., Boime, I, "Granulosa Cells as Hormone Targets: The role of Biologically Active Follicle-Stimulating Hormone in Reproduction" *Rec. Prog. Horm. Res.,* 1989, 45, 209–277.

Current hormonal contraception methods are steroidal and take advantage of long-loop feedback inhibition of gonadotropin secretion, as well as effecting peripheral mechanisms such as sperm migration and fertilization. An alternative strategy for hormonal contraception would be the development of specific antagonists of the receptor for FSH. Such antagonists would disrupt the actions of FSH on follicular development, thus producing the desired contraceptive effect. The utility of this strategy is supported by mechanism of infertility of women with resistant ovary syndrome. The infertility experienced by these women is the result of non-functional FSH receptors (K. Aittomaki, J. L. D. Lucena, P. Pakarinen, P. Sistonen, J. Tapanainnen, J. Gromoll, R. Kaskikari, E. -M. Sankila, H. Lehvaslaiho, A. R. Engel, E. Nieschlag, I. Huhtaniemi, A. de la Chapelle "Mutation in the Follicle-Stimulating Hormone Receptor Gene Causes Hereditary Hypergonadotropic Ovarian Failure" *Cell,* 1995, 82, 959–968). This approach to contraception also appears applicable to men, since idiopathic male infertility seems related to a reduction in FSH binding sites. Moreover, men with selective FSH deficiency are oligo-or azoospermic with normal testosterone levels and present normal virilization. Therefore, orally active FSH antagonists may provide a versatile method of contraception.

Suramin Sodium, is an anticancer agent with a wide variety of activities. Recently suramin was shown to inhibit FSH binding to its receptor (Daugherty, R. L.; Cockett, A. T. K.; Schoen, S. R. and Sluss, P. M. "Suramin inhibits gonadotropon action in rat testis: implications for treatment of advanced prostate cancer" *J. Urol.* 1992, 147, 727–732). This activity causes, at least in part, the decrease in testosterone production seen in rats and humans that were administered suramin (Danesi, R.; La Rocca, R. V.; Cooper, M. R.; Ricciardi, M. P.; Pellegrini, A.; Soldani, P.; Kragel, P. J.; Paparelli, A.; Del Tacca, M.; Myers, C. E, "Clinical and experimental evidence of inhibition of testosterone production by suramin." *J. Clin. Endocrinol. Metab.* 1996, 81, 2238–2246). Suramin is the only non-peptidic small molecule that has been reported to be an FSH receptor binding antagonist.

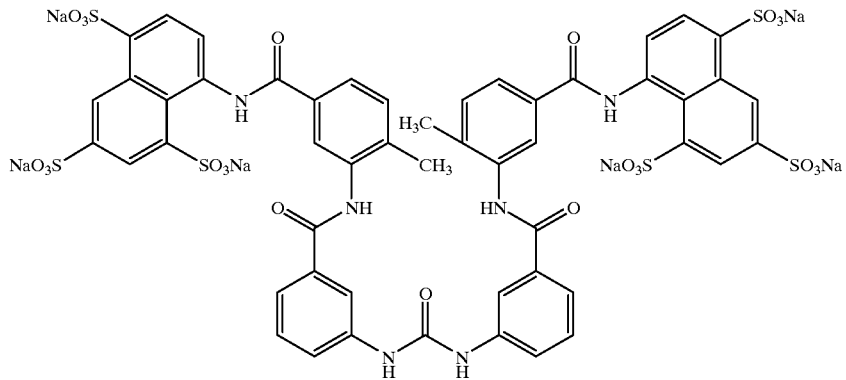

Suramin Sodium

Prior art compounds include those of J. Dannheim, U. Reiher and W. H. Russ (EP 630946) disclosed compounds (A) and (B) as reactive dyes.

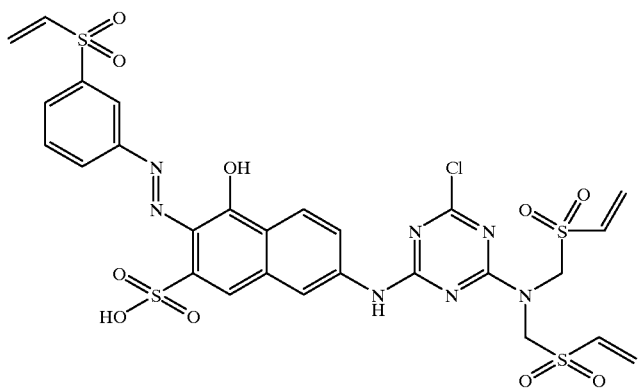
(A)
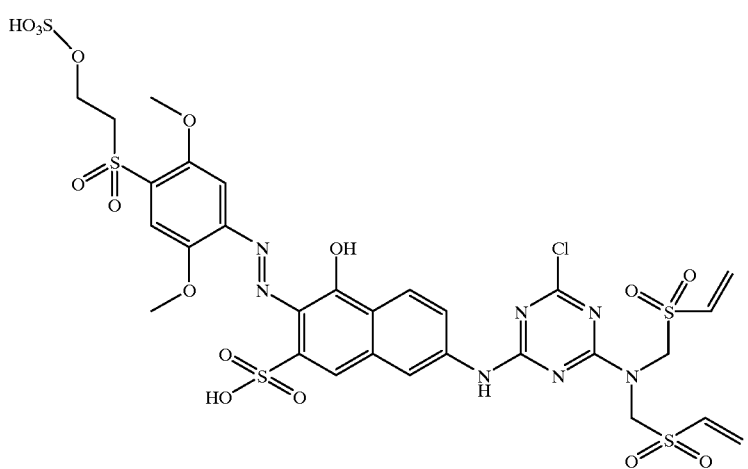
(B)
C. Schumacher and W. H. Russ (EP 675172) disclosed compound (C) as a water soluble reactive dye.
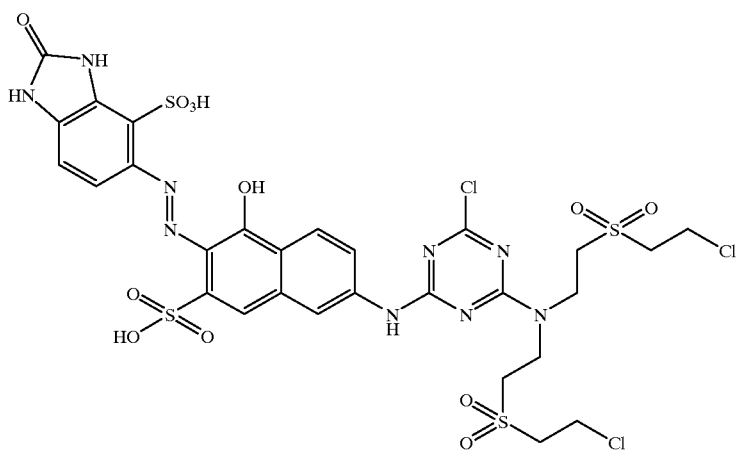
(C)
K. Kunder and K. J. Herd (E( 652262) disclosed compound (D) as a reactive dye.

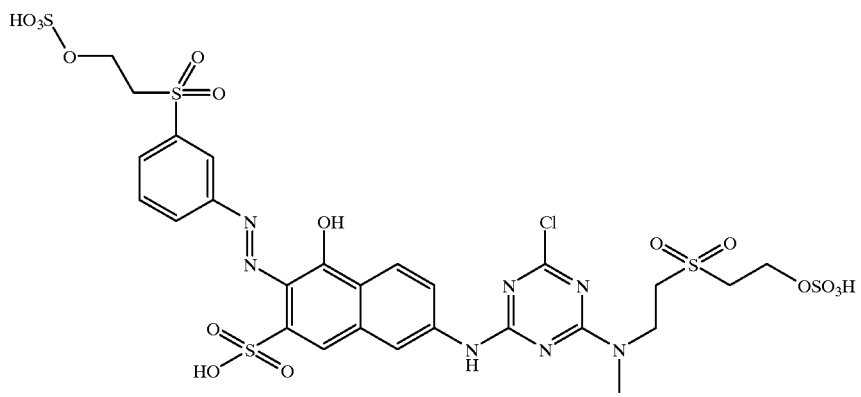
(D)
H. W. Russ, H. Tappe and C. Schumacher (EP 629667) disclosed compound (E) as a reactive dye.
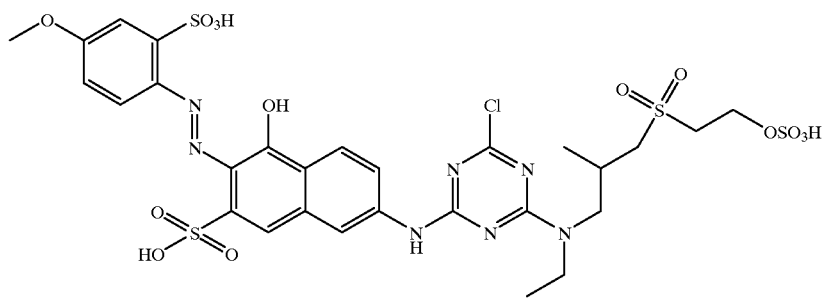
(E)
U. Reither, J. Dannheim and W. H. Russ (EP 624630) disclosed compound (F) as a reactive dye.
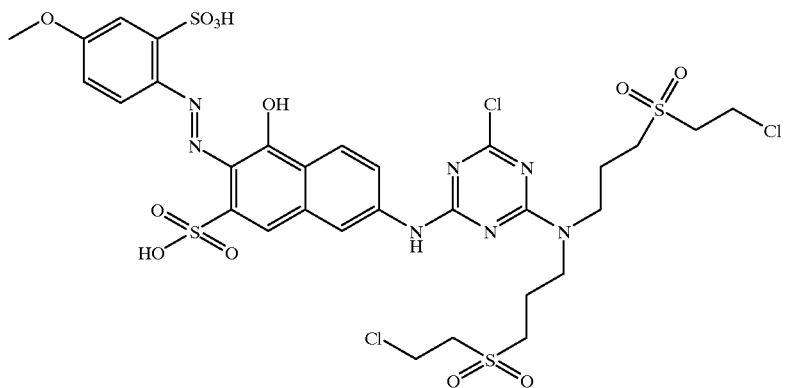
(F)
J. Dannheim and W. H. Russ (EP 513657) disclosed compounds (G) and (H) as reactive dyes.

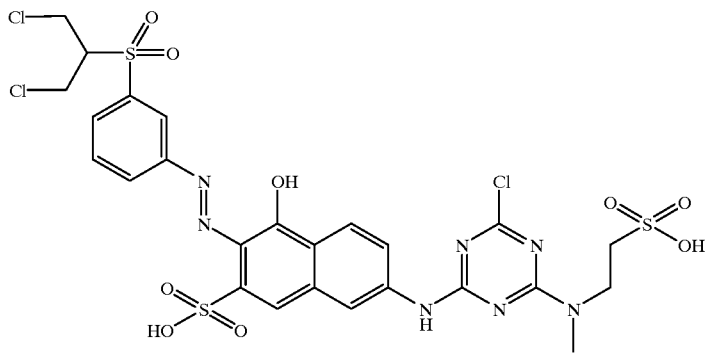
(G)
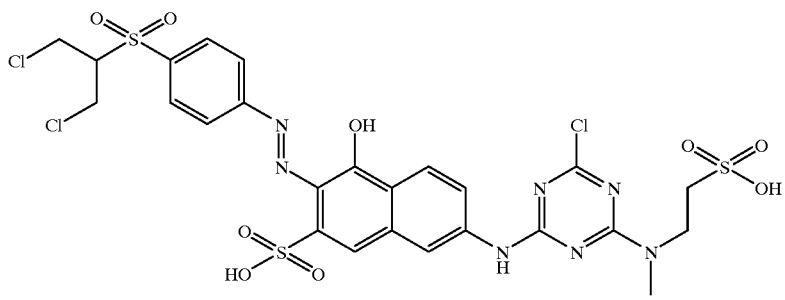
(H)
J. Szadowski and Z. Niewiadomski [*Barwniki, Srodki Pomocnicze* 1996, 40, 55–62] disclosed compounds (I) and (J) as dyes.
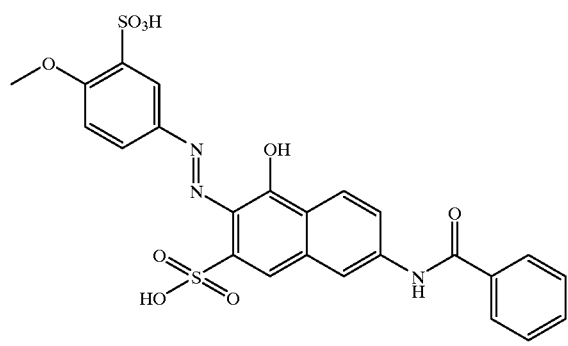
(I)
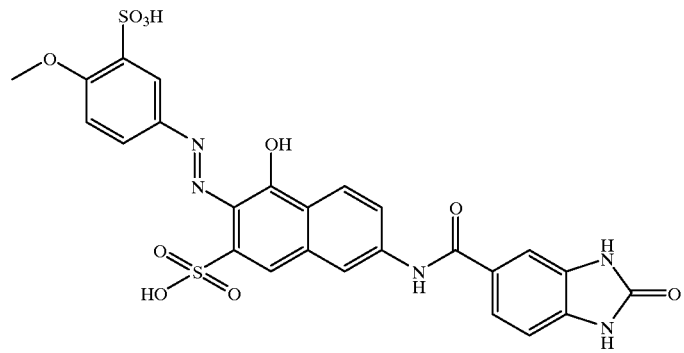
(J)
K. J. Herd, F. M. Stoehr and H. Hermann (EP 272532) disclosed compound (K) as a reactive dye.

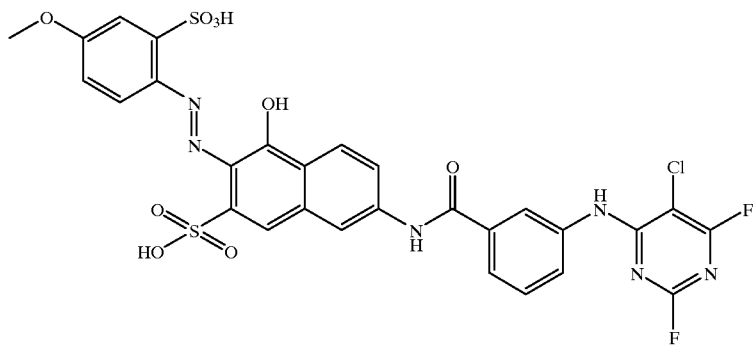
(K)
H. Ischer and H. Siegrist (CH 463656) disclosed compound (L) as a reactive dye.
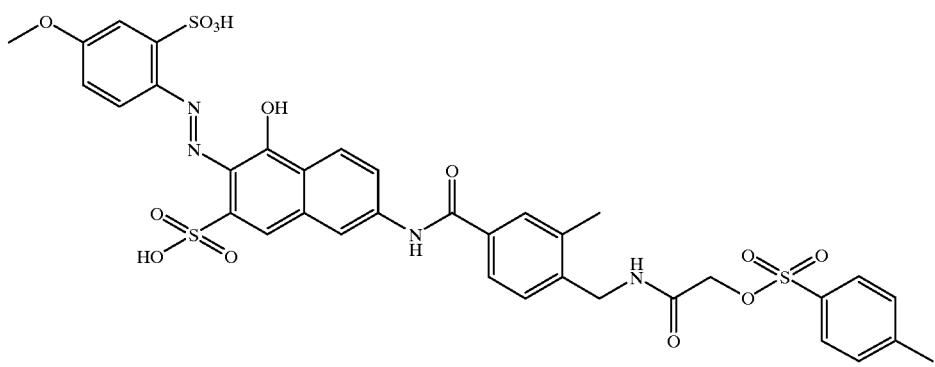
(L)
P. Grandjean (FR 1517223) discolosed compound (M) as a reactive dye.
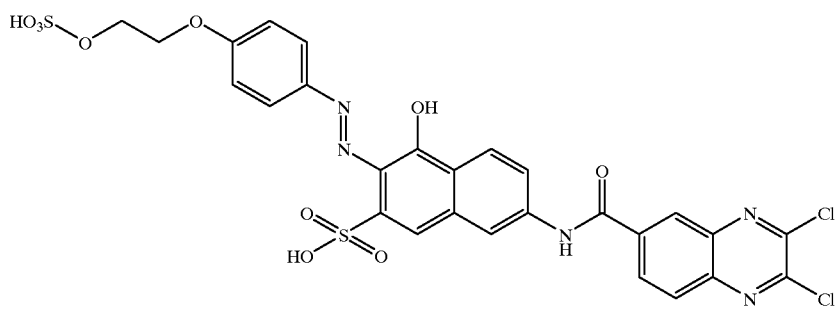
(M)
Compound (N) (CAS registry no 67990-25-4) was disclosed.

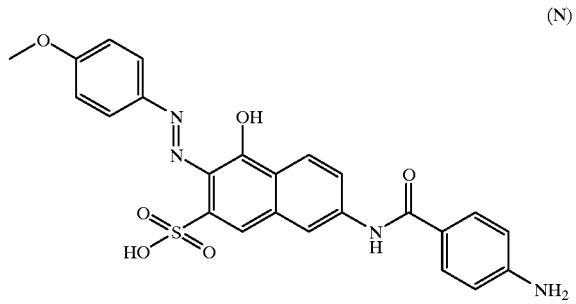

(N)

L. Ruggli (*Helv. Chim. Acta* 1939, 22, 1170–1177 disclosed the compounds of formula (O) and (P).

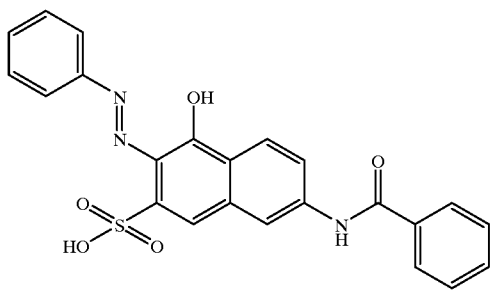

(O)

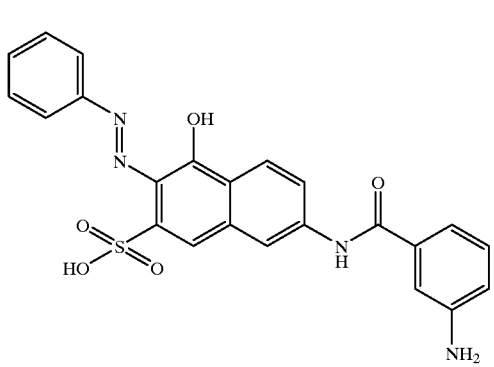

(P)

These prior art compounds do not possess the substitutions on the triazene or benzoyl rings seen in the present compounds of formula (I).

DESCRIPTION OF THE INVENTION

The compounds of this invention antagonize the binding of hFSH to its receptor and block cellular functions of FSH, including the production of second messenger cAMP and estradiol in ovarian and granulosa cells. The compounds of this invention are useful as female and male contraceptive agents.

The compounds useful in this invention have the general formula (I)

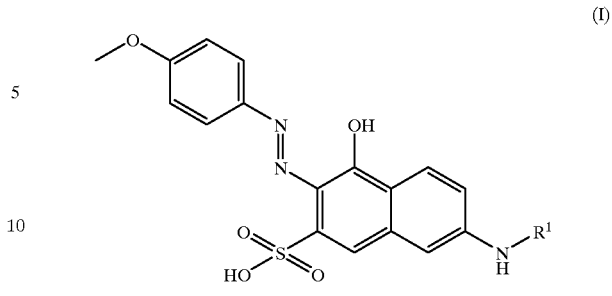

(I)

wherein

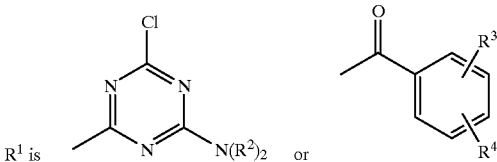

$R^1$ is $R^2$ is $CH_2CH_2CONH$, or $CH_2CH_2OH$;
$R^3$ and $R^4$ are independent substituents from the group including H, $-N(CH_3)_2$, or $-OCH_3$;
or pharmaceutically acceptable salts thereof.

Among the preferred compounds of this invention include the compounds of formula (Ia), below:

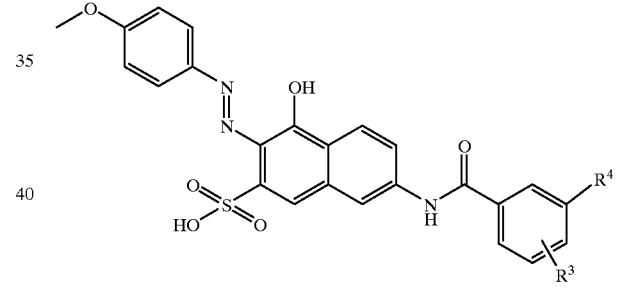

(Ia)

wherein $R^3$ and $R^4$ are independent substituents, as defined above, and:

when $R^3$ is from the group including H or 4-$N(CH_3)_2$; $R^4$ is H;

and when $R^3$ is 4-$OCH_3$ or 5-$OCH_3$; $R^4$ is $-OCH_3$;
or pharmaceutically acceptable salts thereof.

Other preferred compounds of this invention include the compounds of formula (Ib), below

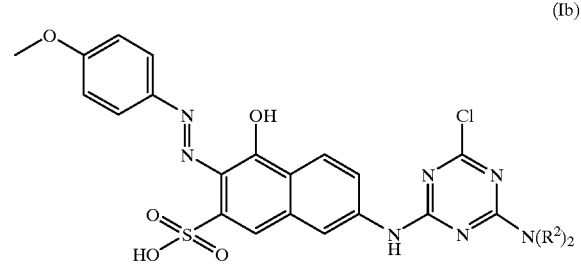

(Ib)

wherein R² is —CH₂CH₂CONH₂ or —CH₂CH₂OH;
or pharmaceutically acceptable salts thereof.

Among the most preferred compounds in this invention are:

7-{4-[bis-(2-carbamoyl-ethyl)-amino}-6-chloro-[1,3,5]-triazin-2-ylamino}-4-hydroxy-3-(4-methoxy-phenylazo)-naphthalene-2-sulfonic acid (Example 3, 9);

7-{4-[bis-(2-hydroxy-ethyl)-amino}-6-chloro-[1,3,5]-triazin-2-ylamino}-4-hydroxy-3-(4-methoxy-phenylazo)-naphthalene-2-sulfonic acid (Example 11);

7-(3,4-dimethoxy-benzoylamino)-4-hydroxy-3-(4-methoxy-phenylazo)-naphthalene-2-sulfonic acid (Example 19);

7-benzoylamino-4-hydroxy-3-(4-methoxy-phenylazo)-naphthalene-2-sulfonic acid (Example 16);

7-(3,5-dimethoxy-benzoylamino)-4-hydroxy-3-(4-methoxy-phenylazo)-naphthalene-2-sulfonic acid (Example 14);

7-(4-dimethylamino-benzoylamino)-4-hydroxy-3-(4-methoxy-phenylazo)-naphthalene-2-sulfonic acid (Example 12);

or the pharmaceutically acceptable salts thereof.

This invention also comprises a method of inducing contraception in a male or female mammal, the method comprising administering to the mammal in need thereof a pharmaceutically effective amount of a compound of this invention, or a pharmaceutically acceptable salt thereof. The compounds of this invention may be administered orally or parenterally, neat or in combination with conventional pharmaceutical carriers and/or excipients. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific psychosis must be subjectively determined by the attending physician. The variables involved include the specific psychosis or state of anxiety and the size, age and response pattern of the patient. In therapeutic treatment, projected daily dosages of the compounds of this invention are 0.1–500 mg/kg for oral administration.

The compounds of this invention can be conveniently prepared according to the methods outlined in the schemes below. Unless otherwise noted, R¹, R², R³, and R⁴ are as defined above.

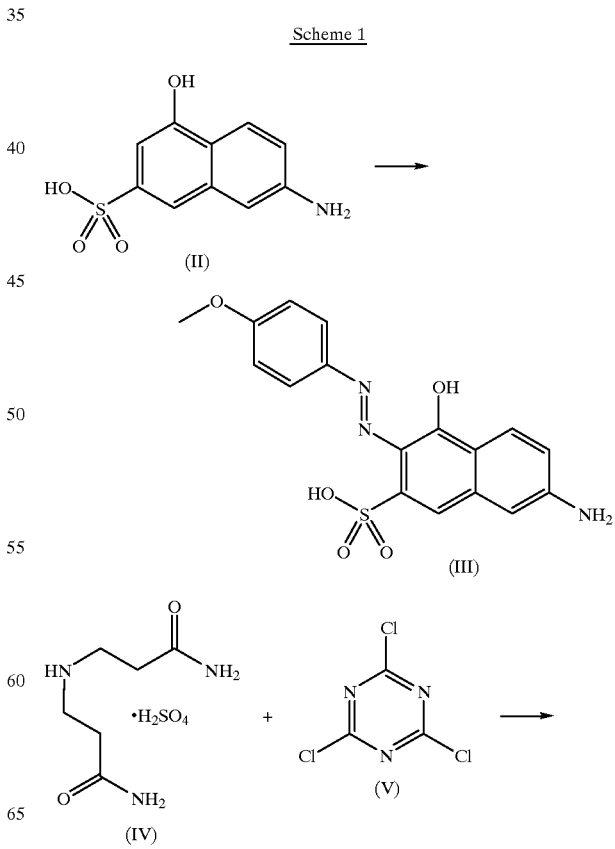

Scheme 1

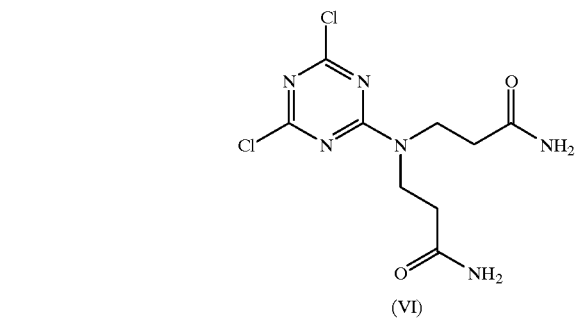

(VI)

(III) + (VI) →

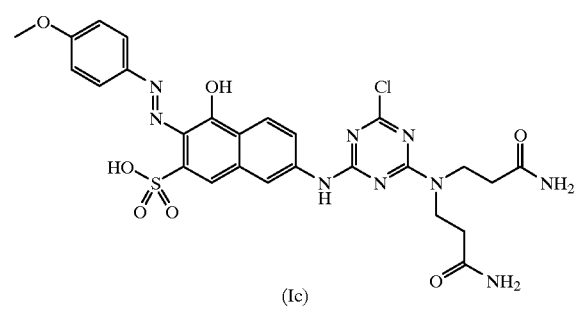

(Ic)

Scheme 2

(III) →

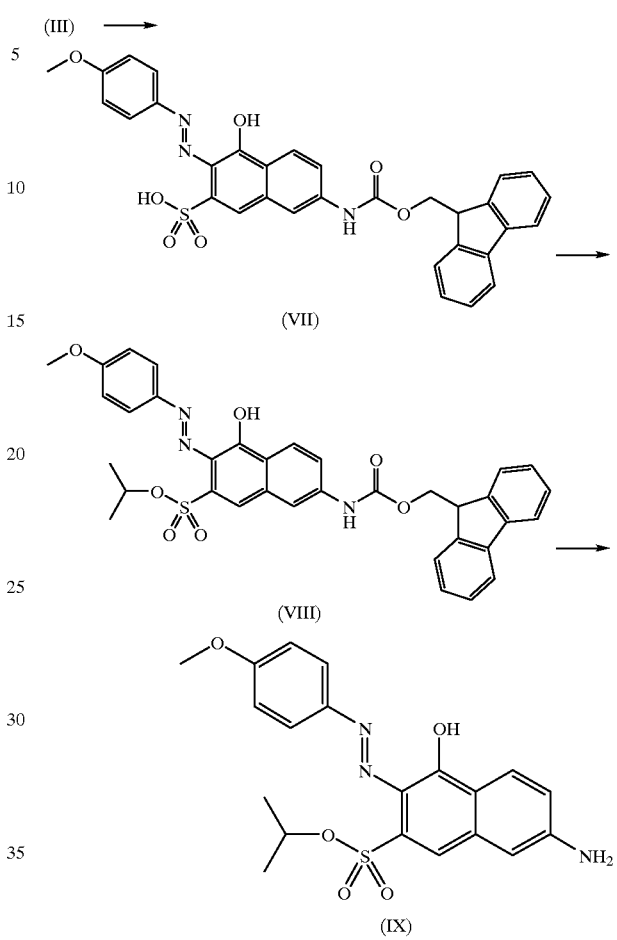

According to Scheme 1, p-anisidine is treated with one or more equivalents of a mineral acid such as hydrochloric acid or sulfuric acid in an aqueous solvent with or without an organic co-solvent such as TBF or ethanol. One or slightly more than one equivalent of an alkali metal nitrite such as sodium nitrite is then added. The reaction temperature range is generally between −10 and 10° C. After an additional 10 minute to two hours, the compound of formula (II) is added. This compound is most conveniently added to the reaction mixture as an aqueous solution of its alkali metal salt, such as its sodium salt. The pH of the reaction mixture is then maintained between pH 8 to 9 using an alkali metal base such as sodium hydroxide and the reaction mixture is stirred for ½ to ten hours. The reaction mixture is then acidified with a mineral acid such as hydrochloric acid to pH 6 to 8 to provide the compound of formula (III).

3,3-Iminodipropionitrile is converted to the sulfuric acid salt of the bisamide of formula (IV). This compound of formula (IV) is dissolved in water and the pH is adjusted to 6 to 7 with an alkali metal base such as sodium hydroxide. While maintaining the temperature range between −10 and 10° C. and the pH range from 6 to 7 using an alkali metal base such as sodium hydroxide, a solution of one molar equivalent of cyanuric chloride in acetone is added and the reaction is allowed to stir for ½ to five hours at −10 to 10° C. temperature range to provide, in situ, the compound of formula (VI). To this reaction mixture containing the compound of formula (VI) is added an aqueous solution or suspension of the compound of formula (III). The pH is adjusted and maintained in the range from 6 to 7 using an alkali metal base such as sodium hydroxide and the reaction mixture is stirred at ambient temperatures for one to 48 h and then heated to 50 to 80° C. for a period of one to twelve hours to provide the compound of formula (Ic) as a crude mixture with the purity of the compound of formula (Ic) in this mixture being generally between 35 and 70%. Preparative BHLC is generally the most effective means to purify the crude mixture to provide the compound of formula (Ic) in greater purity (>90%). Alternative means of providing the compound of formula (Ic) are shown in Schemes 2 and 3.

According to Scheme 2, the compound of formula (III) can be protected as its FMOC derivative using standard methods. For example, the compound of formula (III) or an alkali metal salt, such as the sodium salt of this compound is treated with one or more equivalents of an alkali metal carbonate, such as sodium carbonate, and one or more equivalents of 9-fluorenylmethyl chloroformate in a lower alcohol solvent such as methanol at temperature ranging from 0 to 40° C. to afford the FMOC protected compound of formula (VII).

The compound of formula (VII) can then be esterified on the sulfonic acid moiety using a procedure similar to sulfonic acid esterification methods of A. A Padmapriya, G. Just and N. G. Lewis *Synthetic. Comm.* 1985, 15, 1057–1062 and J. I. Trujillo and A. S. Gopalan *Tetrahedron Lett.* 1993, 34, 7355–7358 except employing tri-isopropylorthoformate as the esterification reagent. The acid form of the compound of formula (VII) is heated with one or more equivalents of tri-isopropylorthoformate in a suitable solvent such as dioxane at temperatures ranging from 40 to 100° C. over a period ranging from one to 48 h to produce the isopropyl ester of formula (VIII).

The FMOC group of the compound of formula (VIII) can be removed using standard conditions, most notably using one or more equivalents of an organic amine base such as piperidine in a suitable solvent such as DMF or TBF to provide the amine of formula (IX). This reaction is most conveniently done at the temperature range of 0 to 40° C. over a time period of 5 minutes to 10 h.

Scheme 3

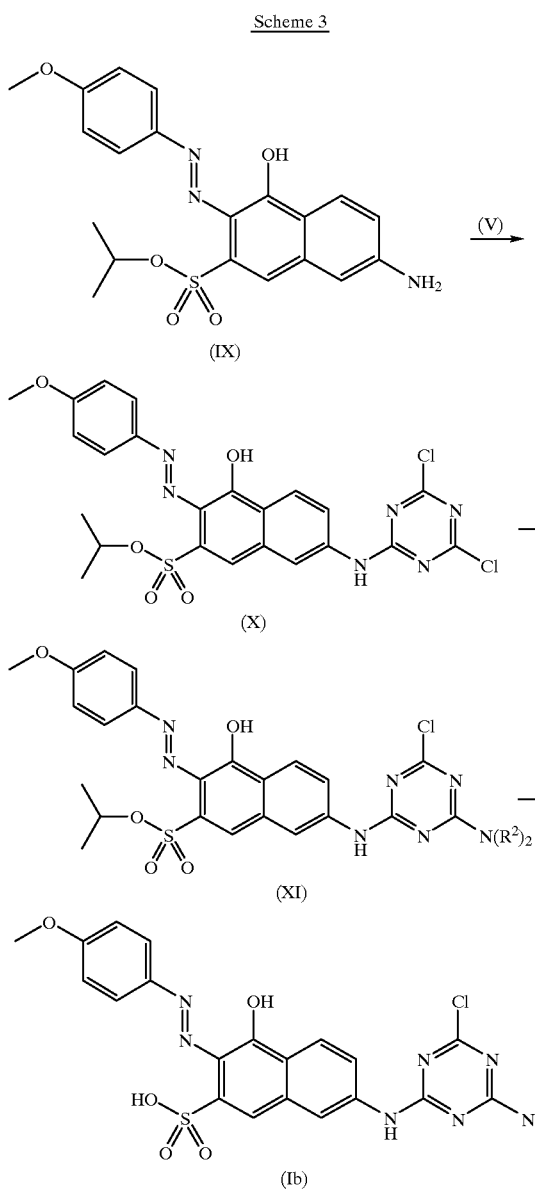

Scheme 4

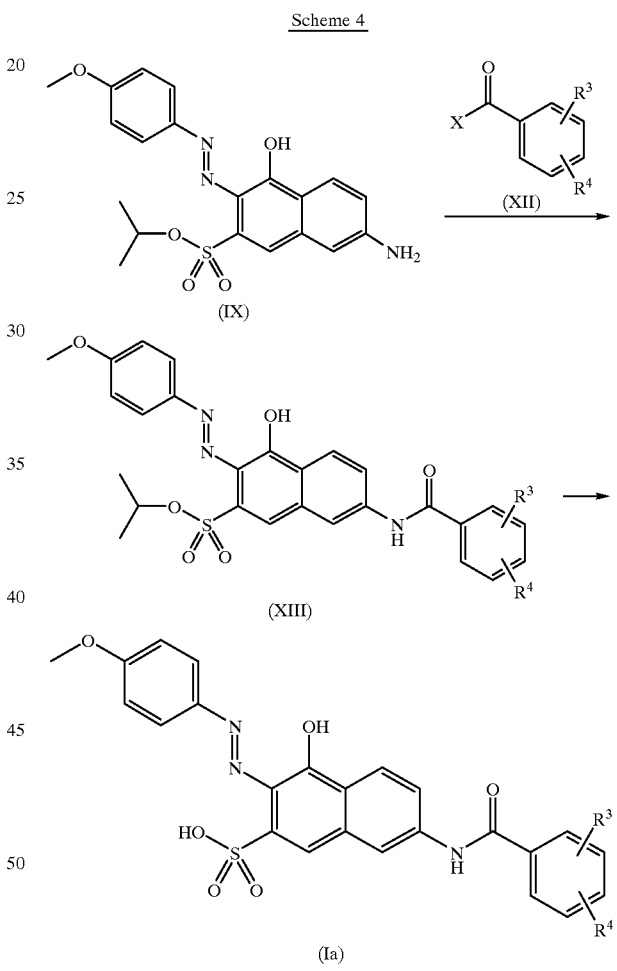

According to Scheme 3, the compound of formula (IX) can be reacted with one or more equivalents of commercially available cyanuric chloride in the presence of a one or more equivalents of a base, such as an alkali metal carbonate or hydroxide like sodium carbonate or potassium hydroxide, or an organic amine base such as pyridine or diisopropylethylamine to provide the compound of formula (X). This reaction is most conveniently done in a suitable solvent such acetone at temperatures ranging from −10 to 10° C. over a period of 20 minutes to 10 h.

The compound of formula (X) can be reacted with one or more equivalents of a commercially available secondary organic amine of the formula $HN(R^2)_2$ to afford the compound of formula (XI). Generally one or more equivalents of a base, such as an alkali metal bicarbonate or hydroxide like sodium bicarbonate or potassium hydroxide, or an organic amine base such as pyridine or diisopropylethylamine can also be added to the reaction mixture in order to force the reaction to completion by reacting with the excess HCl generated. This reaction is most conveniently performed in an organic solvent such as acetone or THF generally using water as a co-solvent over the temperature range of 0 to 50° C. over a time period of 1 h to 48 h.

The compound of formula (X) can then be deesterified to provide the compound of formula (Ib). This is most conveniently accomplished using one or more molar equivalents of a alkali metal halide such as sodium iodide or lithium bromide in a suitable solvent such as acetone or 2-butanone with or without a co-solvent such as water at temperatures ranging from 0 to 100° C. and over a time period of one to 48 h. Other methods to effect deesterification to provide the compound of formula (Ib) include reacting the compound of formula (X) with one or more equivalents of an organic base such as piperidine and dimethylaminopyridine in an organic solvent such as THF or DMF at temperatures ranging from 20 to 120° C. over periods of 1 h to 64 h.

According to Scheme 4, the compound of formula (IX) can be reacted with a benzoic acid chloride of formula (XII, X=Cl) to produce the compound of formula (XIII). This reaction is usually performed in the presence of one or more equivalents of a organic amine base such as diisopropylethyl amine or one or more equivalents of an inorganic base such as sodium bicarbonate. Suitable solvents for this transformation include halocarbon solvents such as dichloromethane, TBF or DMF. This reaction is usually performed in the temperature range including 0 to 50° C. over a period of 30 minutes to 48 hours. The benzoic acid chloride of formula (XII) is either commercially available or readily prepared from commercially available benzoic acid of formula (XII, X=OH). Standard reagents and conditions are used to effect the benzoic acid to benzoic acid chloride transformation, for example, treatment of the benzoic acid of formula (XII, X=OH) with one or more equivalents of oxalyl chloride in the presence of a catalytic amount of DMF in a halocarbon solvent, such as dichloromethane, at temperatures ranging from 0 to 35° C. will afford the benzoic acid chloride of formula (XII, X=Cl).

Alternatively, the compound of formula (XIII) can be prepared from the compound of formula (IX) and the benzoic acid of formula (XII, X=OH) using standard amidation and peptide coupling conditions. For instance, treatment of the benzoic acid of formula (XII, X=OH) with one or more equivalents of a commercially available carbodiimide such as dicyclohexylcarbodiimide (DCC) or 1-(3-dimethylamino)propyl)-3-ethylcarbodiimide hydrochloride (EDCI) and subsequent reaction with the compound of formula (IX) results in the formation of the compound of formula (1a). The reaction is conveniently performed with or without one or more equivalents of commercially available additive N-hydroxybenzotriazole (HOBT), and with or without one or more equivalents of an organic base such as triethylamine or diisopropylethylamine or an inorganic base such as sodium bicarbonate. Solvents generally useful include halocarbon solvents such as dichlormethane, THF or DMF.

The compound of formula (XIII) can then be deesterified to provide the compound of formula (Ia). This is most conveniently accomplished using one or more molar equivalents of a alkali metal halide such as sodium iodide or lithium bromide in a suitable solvent such as acetone or 2-butanone with or without a co-solvent such as water at temperatures ranging from 0 to 100° C. and over a time period of one to 48 h. Other methods to effect deesterification to the compound of formula (Ia) include reacting the compound of formula (XIII) with one or more equivalents of an organic base such as piperidine and dimethylaminopyridine in an organic solvent such as THF or DMF at temperatures ranging from 20 to 120° C. over periods of 1 h to 64 h.

The following nonlimiting examples further illustrate this invention.

EXAMPLE 1

7-Amino-4-hydroxy-3-(4-methoxy-phenylazo)-naphthalene-2-sulfonic Acid, Sodium Salt At room temperature under $N_2$ atmosphere, 5N HCl (25 mL) was added to a stirred suspension of p-anisidine (3.09 g, 25 mmol) in 100 mL water. To the clear solution at 0° C., a sodium nitrite solution (1.9 g, 27 mmol) in 6 mL water was added over a period of 15 minutes and the reaction mixture was stirred for an additional 15 minutes. The mixture was added dropwise into a solution of 7-amino-4-hydroxy-2-naphthalene sulfonic acid, sodium salt (6.95 g, 25 mmol) in 250 mL water and 6 mL 5N NaOH. Additional 5N NaOH was added as needed to maintain the reaction mixture pH 8–9. After addition was completed, the red dark mixture was stirred at pH 9 for one hour. The pH of the reaction mixture was then slowly adjusted to pH 7.5 with 5N HCl over a period of 2 hours. The reaction mixture was then diluted with a saturated NaCl solution (250 mL) and allowed to stand at 5° C. for 18 hours. The resulting fine red crystals were collected, rinsed with water and dried at 70° C. in vacuum to afford the title product as a red solid (10.4 g): NMR (DMSO-$d_6$): δ 3.80 (s, 3H, OCH$_3$), 6.24 (s, 2H, NH$_2$) 6.63 (d, J=5.5 Hz, 1H, aromatic), 6.69 (d, J=5.5 Hz, 1H, aromatic), 7.01 (m, 2H, aromatic), 7.21 (s, 1H, aromatic), 7.63 (m, 2H, aromatic), 7.91 (d, J=20 cps, 2H, aromatic) ppm; MS (ESI): [M−H] at m/z 372; UV (MeOH): $\lambda_{max}$ 234.5 (e 19026), 304 (e 12842) nm.

EXAMPLE 2

Bis-(2-carbamoyl-ethyl)-amine, Sulfuric Acid Salt

At −10° C., water (14 mL) was treated with concentrated sulfuric acid (100 mL). To the acidic solution at −10° C., 3,3-iminodipropionitrile (39 g, 0.317 mol) was added over a period of 30 minutes. The reaction mixture was stirred at 0° C. for 2 hours and at room temperature for one hour. It was then poured at room temperature into absolute ethanol (4 L) over a period of 30 minutes then cooled at 5° C. for 18 hours. The white crystalline material was collected and dried at 100° C. in vacuum to afford the title product as a white solid (69 g, 85%): mp 152–156° C.: NMR (DMSO-$d_6$): δ 2.49 (m, 4H, CH$_2$CO), 3.01 (m, 4H, CH$_2$NH), 7.10 (s, 2H, NH$_2$), 7.50 (s, 2H, NH$_2$).

EXAMPLE 3

7-{4-[Bis-(2-carbamoyl-ethyl)-amino]-6-chloro-[1,3,5]-triazin-2-ylamino)-4-hydroxy-3-(4-methoxy-phenylazo)-napthalene-2-sulfonic Acid, Sodium Salt An aqueous solution of bis-(2-carbamoyl-ethyl)-amine, sulfuric acid salt (Example 2, 8.76 g, 34 mmol) in 65 mL of water was adjusted to pH 6.5 with 50% NaOH solution and cooled to 0° C. To this solution at 0° C., a solution of cyanuric chloride (6.27 g, 34 mmol) in 55 mL acetone was added while maintaining the mixture at pH 6.5 with addition of a sodium carbonate aqueous solution. After stirring at 0° C. for 1.5 hours, the white suspension was treated with 7-amino-4-hydroxy-3-(4-methoxy-phenylazo)-naphthalene-2-sulfonic acid, sodium salt (Example 1, 13.4 g, 34 mmol) in 120 mL water while maintaining between pH 6.3–6.5. The resulting red suspension was stirred at room temperature for 20 hours and then heated at 65° C. for 6 hours while keeping the pH at 6.5. The mixture was poured into 2-propanol (1.8 L) then cooled at 0° C. for ½ hour. The red solid ppt was collected, rinsed with 2-propanol and dried at 75° C. in vacuum to afford 26.1 g the crude product as a red solid. This crude product contained the title compound in about 40% purity by BPLC analysis. The crude product (10 g) was purified by HPLC using the following procedure.

One gram of the crude sample was dissolved in 200 mL water and approximately 10 mL MeOH. To this mixture was added Dowex 50 X 8; ion exchange resin; 20–50 mesh; Na(+) form (Fluka), then 1N NaOH (1.5 mL), and the mixture was stirred with heating (35–40° C.) for approximately 30 minutes. The mixture was filtered and the filtrate washed with water (3×50 mL). The solution containing the sodium salt of the title compound was reduced in volume in vacuo; the residue was redissolved in a minimum volume of water, frozen and the frozen sample was lyophilized (overnight) to dryness.

BPLC samples were prepared by dissolving 50 mg of this lyophilized sample into 1 mL of 50 mM TEAA, then filtering this solution with a Glass Fiber Acrodisc (*Gelman Sciences*). Repeated injections of the 50 mg/mL solution onto a reversed-phase column (Primesphere 10 C18-HC, 50 mm id×250 mm length) were made using the following mobile-phase conditions: Step gradient: 55:45 (Methanol: 50 mM triethylammonium acetate; pH=7 for 13 minutes and 80:20 for 4 minutes;. Monitoring of UV detection was at 254 nm, fractions were collected, and subsequently analyzed for purity by analytical HPLC under similar mobile phase conditions. Purified fractions with identical HPLC retention volume were combined, the solvent was removed in vacuo to provide the triethylammoniuim salt of the title compound in 20–25% from the crude. The sodium salt was prepared in batches. Approximately 400–500 mg of the BPLC-purified triethylammonium salt was dissolved in approximately 175 mL water, added to 100 mL of Toyopearl SP-650C strong cation exchange gel (Na+ form), stirred for approximately 40 minutes, and vacuum filtered. The ion exchange support was subsequently washed with approximately 350 mL water, and the combined solutions were reduced in volume in vacuo to provide the title compound as a red solid. The yield of conversion from the triethylammonium to the sodium salt of the title compound was approximately 90–95%. The overall yield of the crude mixture to purified material was approximately 15–20%. BPLC: 97.5% purity; MS (ESI): [M–H]$^-$ at m/z 642; UV (H$_2$O): $\lambda_{max}$ 260 (e 16753), 359 (e 23100) nm. See Example 9 for additional analytical information on this compound.

EXAMPLE 4

7-(H-Fluorene-9-ylmethoxycarbonylamino)-4-hydroxy-3-(4-methoxy-phenylazo)-napthalene-2-sulfonic Acid 7-Amino-4-hydroxy-3-(4-methoxy-phenylazo)-napthalene-2-sulfonic acid (Example 1, 10 g, 25 mmol) was suspended in methanol (200 mL) under N$_2$ and sodium carbonate (7.1 g, 68 mmol) was added. The 9-fluorenylmethyl chloroformate (16.4 g, 63 mmol) was added portionwise. The suspension was allowed to stir overnight, and the following morning, the reaction was complete. HCl/dioxane (30 mL, 120 mmol) was added and the suspension was allowed to stir for 1 h. The solvent was removed (carefully) under reduced pressure, and the concentrate was triturated with ether for 2 h. This mixture was filtered, providing the title compound as a crude product (~60% pure, 24 g total weight): mp>250° C.; NMR (DMSO-d6): $\delta$ 16.20 (s, 1H), 10.25 (s,1H), 8.16 (d, J=9 Hz, 1H), 7.96 (d, J=9 Hz, 2H), 7.77 (m, 5H), 7.60 (m, 1H), 7.39 (m, 5H), 7.07 (d, J =9 Hz, 2H), 4.56 (d, J=3 Hz, 2H), 4.37 (t, J=3 Hz, 1H), 3.83 (s, 3H); MS (ES-NEG): [M–H] 594.

EXAMPLE 5

7-(H-Fluorene-9-ylmethoxycarbonylamino)-4-hydroxy-3-(4-methoxy-phenylazo)-napthalene-2-sulfonic acid isopropyl Ester Using a method similar to that of A. A Padmapriya, G. Just and N. G. Lewis *Synthetic Comm.* 1985, 15, 1057-1-62 and J. I. Trujillo and A. S. Gopalan *Tetrahedron Lett.* 1993, 34, 7355–7358, 7-(H-Fluorene-9-yl-methoxycarbonylamino)-4-hydroxy-3-(4-methoxy-phenylazo)-napthalene-2-sulfonic acid crude (Example 4, 24 g, about 60% pure, ~25 mmol) was suspended in dioxane (200 mL) and triisopropylorthoformate (26.74 mL, 120 mmol) was added. The reaction mixture was heated to 60° C. and allowed to stir overnight. The following morning, the dioxane was filtered and saved. The solid was was triturated with dichloromethane and refiltered twice. The solvents from the combined dichloromethane and dioxane phases were removed under reduced pressure to provide the title compound (12.98 g, 20 mmol, 80% based on the starting material in Example 4) as a red solid: mp=135–142° C.; NMR (DMSO-d$_6$): $\delta$ 16.20 (s, 1M), 10.25 (s, 1H), 8.26 (d, J=9 Hz, 1H), 7.96 (m, 3H), 7.77 (m, 5H), 7.60 (m, 6H), 7.39 (m, 4H), 7.07 (d, J=9 Hz, 2H), 4.81 (m, 1H), 4.56 (d, J=3 Hz, 2H), 4.37 (t, J=3 Hz, 1H), 3.83 (s, 3H),1.26 (d, J=3 Hz, 6H); MS (ES-Neg): [M–H] 636; Anal. Calc. for C$_{35}$H$_{31}$N$_3$O$_7$S: C, 65.92, H, 4.90, N, 6.59. Found: C, 65.25, H, 4.81, N, 6.55.

EXAMPLE 6

7-Amino-4-hydroxy-3-(4-methoxy-phenylazo)-napthalene-2-sulfonic acid isopropyl Ester 7-(H-Fluorene-9-ylmethoxycarbonylamino)-4-hydroxy-3-(4-methoxy-phenylazo)-napthalene-2-sulfonic acid isopropyl ester (Example 5, 19 g, 30 mmol) was dissolved in DMF (50 mL) and piperidine (2 mL, 40 mmol) was added. Within 1 h, the reaction was complete. The reaction mixture was partitioned between ethyl acetate and brine to remove DMF. After the emulsion settled, The ethyl acetate layer was washed with 1N HCl to remove piperidine. The ethyl acetate was removed under reduced pressure. The solid was washed with water and filtered. The solid was triturated in hexane to provide the title compound (11.12 g, 26.7 mmol, 87%), as a red solid: NM (DMSO-d$_6$): $\delta$ 16.25 (s, 1H), 8.16 (d, J=9 Hz, 1H), 7.96 (m, 3H), 7.20 (d, J=9 Hz, 2H), 6.95 (m, 2H), 6.65 (s, 2H), 4.81 (m, 1H), 3.86 (s, 3H), 1.32 (d, J=3 Hz, 6H); MS (FAB): [M+Na+] 438, [M+] 415; Anal. HPLC: 98% pure. Anal. Calc. for C$_{20}$H$_{21}$N$_3$O$_5$S: C, 57.82, H, 5.09, N, 10.11. Found: C, 56.76, H, 4.90, N, 9.72.

EXAMPLE 7

7-(4,6-Dichloro-[1,3,5]-triazin-2-ylamino)-4-hydroxy-3-(4-methoxy-phenylazo)-napthalene-2-sulfonic Acid Isopropyl Ester 7-Amino-4-hydroxy-3-(4-methoxy-phenylazo)-napthalene-2-sulfonic acid isopropyl ester Example 6, 10 g, 24 mmol) was suspended in acetone (120 mL) and cyanuric chloride (6.65 g, 36 mmol) was added. Saturated sodium bicarbonate (3 mL) was then added to the suspension. After 3 h, the reaction mixture was filtered, to provide the title compound (11.1 g, 19.7 mmol, 82%) as a red solid: NMR (DMSO-d$_6$): $\delta$ 16.30 (s, 1H), 11.86 (s, 1H), 8.25 (d, J=9 Hz, 1H), 8.08 (s, 1H), 7.96 (d, J=9 Hz, 1H), 7.87 (s, 1H), 7.76 (d, J=9 Hz, 2H), 7.15 (d, J=9 Hz, 2H), 4.61 (m, 1H), 3.92 (s, 3H), 1.31 (d, J=3 Hz, 6H); MS (° FAB): 2 chlorine isotope pattern, [M+Na+] 585, [M+H+] 563; Anal. Calc. for C$_{23}$H$_{20}$Cl$_2$N$_6$O$_5$S: C, 49.03, H, 3.58, N, 14.92. Found: C, 47.66, H, 3.29, N, 14.31.

EXAMPLE 8

7-{4-[Bis-(2-carbamoyl-ethyl)-amino]-6-chloro- [1,3,5]-triazin-2-ylamino)-4-hydroxy-3-(4-methoxy-phenylazo)-napthalene-2-sulfonic Acid Isopropyl Ester 7-(4,6-Dichloro-[1,3,5]-triazin-2- ylamino)-4-hydroxy-3-(4-methoxy-phenylazo)-napthalene-2-sulfonic acid isopropyl ester Example 7, 3.5 g, 6.2 mmol) was suspended in acetone (200 mL) and cooled to 0° C. In a separate flask, bis-(2-carbamoyl-ethyl)-amine, sulfuric acid salt Example 2, 6.37 g, 24.8 mmol) was neutralized in a 1 N NAOH solution (50.4 mL). The neutralized amine was added dropwise via an addition funnel to the stirring suspension of the ester. The reaction mixture was allowed to warm to room temperature, and was stirred overnight. After 15 h, the reaction mixture was filtered. The solid was suspended in water and stirred for 0.5 h. The solid was filtered, and the solid was suspended in 10% methanol/ethyl acetate for 0.5 h. The solid was filtered again, and washed twice with ether. The solid was dried under vacuum, to provide the title compound (3.58 g, 4.7 mmol, 76%) as a red solid: NMR (DMF-d$_7$): $\delta$ 10.59 (s, 1H), 8.45 (d, J=9 Hz, 2H), 8.28 (d, J=9 Hz, 1H), 8.01 (m, 1H), 7.92 (d, J=9 Hz, 2H), 7.60 (d, J=16 Hz, 2H), 7.19 (d, J=9 Hz, 2H), 6.87 (d, J=9 Hz, 2H), 4.96 (m, 1H), 4.00 (m, 2H), 3.92 (m, 5H), 2.70 (m, 2H), 2.67 (m, 2H), 1.31 (d, J=3 Hz, 6H); MS (ES-NEG): [M+H+] 684; Anal. Calc. for $C_{23}H_{20}Cl_2N_6O_5S$: C, 50.76, H, 4.70, N, 18.37. Found: C, 49.48, H, 4.55, N, 17.46.

EXAMPLE 9

7-{4-[Bis-(2-carbamoyl-ethyl)-amino]-6-chloro-[1,3,5]-triazin-2-ylamino)-4-hydroxy-3-(4-methoxy-phenylazo)-napthalene-2-sulfonic Acid, Sodium Salt This is the same compound produced in Example 3 using a different procedure. 7-{4-[Bis-(-carbamoyl-ethyl)-amino]-6-chloro-[1,3,5]-triazin-2-ylamino)-4-hydroxy-3-(4-methoxy-phenylazo)-napthalene-2-sulfonic acid isopropyl ester (Example 8, 4 g, 5.8 mmol) was suspended in 2-butanone (500 mL) and sodium iodide (1.31 g, 8.8 mmol) was added. The reaction mixture was allowed to stir at 60° C. for 48 h. The reaction mixture was filtered. The solid was suspended in acetone again and refiltered. The solid was washed with ether and dried in a vacuum oven to provide the title compound (3.65 g, 5.5 mmol, 95%) as a red solid: NMR (DMSO-$d_6$): δ 16.35 (s, 1H), 10.59 (s, 1H), 8.15 (d, J=9 Hz, 1H), 8.01 (s, 1H), 7.96 (m, 1H), 7.70 (d, J=9 Hz, 2H), 7.56 (s, 1H), 7.50 (s, 1H), 7.19 (d, J=9 Hz, 2H), 6.92 (d, J=9 Hz, 2H), 3.92 (m, 5H), 3.70 (m, 2H), 2.50 (m, 2H), 2.37 (m, 2H); MS (F-NEG): [M+H] 642; Analytical HPLC: 93% pure; Anal. Calc. for $C_{23}H_{20}Cl_2N_6O_5S$: C, 46.89, H, 3.78, N, 18.93. Found: C, 44.05, H, 3.39, N, 17.36.

EXAMPLE 10

7-{4-[Bis-(2-hydroxy-ethyl)-amino]-6-chloro-[1,3,5]-triazin-2-ylamino)-4-hydroxy-3-(4-methoxy-phenylazo)-napthalene-2-sulfonic Acid Isopropyl Ester 7-(4,6-Dichloro-[1,3,5]-triazin-2-ylamino)-4-hydroxy-3-(4-methoxy-phenylazo)-napthalene-2-sulfonic acid isopropyl ester (Example 7, 200 mg, 0.36 mmol) in acetone (3 mL) was stirred under nitrogen with sodium carbonate (38 mg, 0.36 mmol). Diethanolamine (35 μL, 40 mg, 0.36 mmol) was added to the stirred suspension, and the reaction mixture was allowed to stir 60 h. The reaction mixture was diluted with hydrochloric acid (3 mL, 1 N) and filtered. The solid was triturated in methanol/ether (1:3) for 1 h and filtered to provide the title compound (179 mg, 0.28 mmol, 79%) as a red solid: NMR (DMSO-$d_6$): δ 16.28 (s, 1H), 10.61 (s, 1H), 8.45 (s, 1H ), 8.30 (d, J=9 Hz, 1H), 7.88 (m, 2H), 7.76 (d, J=9 Hz, 2H), 7.15 (d, J=9 Hz, 2H), 4.78 (m, 1H), 3.90 (m, 13H), 1.23 (d, J=6 Hz, 6H); Analytical HPLC: 87%.

EXAMPLE 11

7-{4-[Bis-(2-hydroxy-ethyl)-amino]-6-chloro-[1,3,5]-triazin-2-ylamino)-4-hydroxy-3-(4-methoxy-phenylazo)-napthalene-2-sulfonic Acid, Sodium Salt 7-{4-[Bis-(2-hydroxy-ethyl)-amino]-6-chloro-[1,3,5]-triazin-2-ylamino)-4-hydroxy-3-(4-methoxy-phenylazo)-napthalene-2-sulfonic acid isopropyl ester (Example 10, 70 mg, 0.11 mmol) was suspended in 2-butanone with sodium iodide (26 mg, 0.17 mmol) under nitrogen. The suspension was heated to 60° C. for 48 h. The 2-butanone was removed, and the concentrate was suspended in 5 mL of acetone. The solid was filtered to provide the title compound (58 mg, 0.09 mmol, 82%) as a red solid: NMR (DMSO-$d_6$): δ 16.38 (s, 1H), 10.51 (s, 1H), 8.21 (m, 2H ), 7.76 (m, 3H), 7.45 (s, 1H), 7.02 (d, J=9 Hz, 2H), 4.64 (m, 2H), 3.90 (m, 11H); MS (F-NEG): [M+H]– 588; Analytical HPLC: 90% ; Anal. Calc. for $C_{24}H_{24}ClN_2O_7S$: C, 48.86, H, 4.10, N, 16.62. Found: C, 45.92, H, 3.95, N, 14.50.

EXAMPLE 12

7-(4-Dimethylamino-benzoylamino)-4-hydroxy-3-(4-methoxy-phenylazo)-napthalene-2-sulfonic Acid, Sodium Salt 7-Amino-4-hydroxy-3-(4-methoxy-phenylazo)-napthalene-2-sulfonic acid isopropyl ester (Example 1, 125 mg, 0.3 mmol ) was dissolved in dichloromethane (3 mL) and diisopropylethylamine (104 μL, 78 mg, 0.6 mmol) was added. p-Dimethylaminobenzoyl chloride (111 mg, 0.6 mmol) was added under nitrogen and the reaction mixture was allowed to stir for 16 h. The solvent was evaporated under a stream of nitrogen. This ester-containing crude solid (35 mg) was suspended in 2-butanone (5 mL) and sodium iodide (14 mg, 0.09 mmol) was added. The reaction mixture was allowed to stir under nitrogen at 60° C. for 48 h. The solvent was removed under a stream of nitrogen, acetone was added and the suspension was filtered to provide the title compound (13 mg, 0.024 mmol) as a red solid: NMR (DMSO-$d_6$): δ 16.31 (s, 1H), 10.28 (s, 1H), 8.28 (d, J=9 Hz, 1H), 8.12 (s, 1H), 7.92 (m, 3H), 7.86 (d, J=9 Hz, 2H), 7.62 (s, 1H), 7.16 (d, J=9 Hz, 2H), 6.85 (d, J=9 Hz, 2H), 3.92 (s, 3H), 2.96 (s, 6H); Analytical HPLC: 71% pure; MS (ES Neg): [M+H] 519.

EXAMPLE 13

7-(3,5-Dimethoxy-benzoylamino)-4-hydroxy-3-(4-methoxy-phenylazo)-napthalene-2-sulfonic Acid Isopropyl Ester 7-Amino-4-hydroxy-3-(4-methoxy-phenylazo)-napthalene-2-sulfonic acid isopropyl ester (Example 6, 200 mg, 0.48 mmol ) was dissolved in dichloromethane (3 mL) and diisopropylethylamine (160 μL, 114 mg, 0.96 mmol ) was added. 3,5 -Dimethoxybenzoyl chloride (111 mg, 0.6 mmol ) was added under nitrogen. The reaction mixture was allowed to stir for 16 h. The suspension was filtered to provide the title compound (110 mg, 0.19 mmol, 40% ) as a red solid: NMR (DMSO-$d_6$): δ 10.72 (s, 1H). 8.46 (s, 1H), 8.32 (d, 9 Hz, 1H), 8.05 ( d, 9 Hz, 1H), 7.80 (d, 9 Hz, 3H), 7.12 (m, 4H), 6.79 (s, 1H), 4.86 (m, 1H), 3.86 (m, 9H), 1.22 (d, 6 Hz, 6H). Analytical HPLC: 87% pure. MS (ES-NEG): [M–H] 578; Anal. Calc. for $C_{29}H_{29}N_3O_8S$: C, 60.09, H, 5.04, N, 7.25. Found: C, 57.60, H, 5.17, N, 6.88.

EXAMPLE 14

7-(3,5-Dimethoxy-benzoylamino)-4-hydroxy-3-(4-methoxy-phenylazo)-napthalene-2-sulfonic Acid 7-(3,5-Dimethoxy-benzoylamino)-4-hydroxy-3-(4-methoxy-phenylazo)-napthalene-2-sulfonic acid isopropyl ester (Example 13, 96 mg, 0.19 mmol) was suspended in 2-butanone (3 mL) and sodium iodide (57 mg, 0.38 mmol) was added. The reaction mixture was allowed to stir under nitrogen at 60° C. for 24 h. The solvent was removed under a stream of nitrogen, acetone was added and the suspension was filtered to provide the title compound (86 mg, 0.17 mmol, 91%) as a red solid: NMR (DMSO-$d_6$): δ 16.34 (s, 1H), 10.47 (s, 1H), 8.27 (d, 9 Hz, 1H), 8.18 (m, 1H), 7.95 (d, J=9 Hz, 1H), 7.83 (d, J=9 Hz, 2H), 7.51 (s, 1H), 7.17 (d, J=3 Hz, 2H), 7.08 (d, J=9 Hz, 2H), 6.74 (t, J=2 Hz, 1H), 3.78 (m, 9H); Analytical HPLC: 94% pure; MS (ES-NEG): [M–H] 536; Anal. Calc. for $C_{26}H_{23}N_3O_8SNa$: C, 55.81, H, 3.96, N, 7.51. Found: C, 52.65, H, 4.45, N, 5.99.

EXAMPLE 15

7-Benzoylamino-4-hydroxy-3-(4-methoxy-phenylazo)-napthalene-2-sulfonic Acid Isopropyl Ester 7-Amino-4-hydroxy-3-(4-methoxy-phenylazo)-napthalene-2-sulfonic acid isopropyl ester (Example 6, 200 mg, 0.48 mmol ) was dissolved in dichloromethane (3 mL) and diisopropylethylamine (160 µL, 114 mg, 0.96 mmol) was added. Benzoyl chloride (85 mg, 0.60 mmol ) was then added under nitrogen. The reaction mixture was allowed to stir for 16 h. The suspension was filtered to provide the title compound (120 mg, 0.23 mmol, 48%) as a red solid: NMR (DMSO-$d_6$): δ 16.25 (s, 1H), 10.81 (s, 1H), 8.52 (m, 1H), 8.37 (d, J=9 Hz, 1H), 8.08 (d, J=9 Hz, 1H), 8.02 (d, J=9 Hz, 2H), 7.81 (d, J=9 Hz, 2H), 7.64 (m, 3H), 7.18 (d, J=9 Hz, 2H), 4.82 (m, 1H), 3.83 (s, 3H), 1.25 (d, J=6 Hz, 6H); Analytical HPLC: 95% pure; MS (ES-NEG): [M–H] 518; Anal. Calc. for $C_{27}H_{24}N_3O_6SNa$: C, 62.42, H, 4.85, N, 8.09. Found: C, 60.61, H, 4.77, N, 7.70.

EXAMPLE 16

7-Benzoylamino-4-hydroxy-3-(4-methoxy-phenylazo)-napthalene-2-sulfonic Acid

7-Benzoylamino-4-hydroxy-3-(4-methoxy-phenylazo-napthalene-2-sulfonic acid isopropyl ester (Example 15, 49 mg, 0.09 mmol) was suspended in 2-butanone (3 mL) and sodium iodide (57 mg, 0.38 mmol) was added. The reaction mixture was allowed to stir under nitrogen at 60° C. for 24 h. The solvent was removed under a stream of nitrogen, acetone was added and the suspension was filtered to provide the title compound (51 mg, 0.08 mmol, 91%) as a red solid: NMR (DMSO-$d_6$): δ 16.30 (s, 1H), 10.68 (s, 1H), 8.26 (d, J=9 Hz, 1H), 8.19 (m, 1H), 8.01 (m, 3H), 7.83 (d, 4H), 7.10 (d, J=9 Hz, 2H), 3.92 (s, 3H); Analytical BPLC: 99% pure; MS (ES-NEG): [M–H] 476; Anal. Calc. for $C_{27}H_{25}N_3O_6S$: C, 57.71, H, 3.63, N, 8.41. Found: C, 52.85, H, 4.44, N, 6.66.

EXAMPLE 17

7-(2,6-Dimethoxy-benzoylamino)-4-hydroxy-3-(4-methoxy-phenylazo)-napthalene-2-sulfonic Acid Isopropyl Ester 7-Amino-4-hydroxy-3-(4-methoxy-phenylazo)-napthalene-2-sulfonic acid isopropyl ester (Example 6, 200 mg, 0.48 mmol) was dissolved in dichloromethane (3 mL) and diisopropylethylamine (160 µL, 114 mg, 0.96 mmol) under nitrogen. 2,6-dimethoxybenzoyl chloride (120 mg, 0.60 mmol) was added and the solution was allowed to stir for 14 h. The resulting suspension was filtered to provide the title -compound (100 mg, 0.17 mmol, 36%) as a red solid: NMR (DMSO-$d_6$): δ 16.30 (s, 1H), 10.81 (s, 1H), 8.35 (s, 1H), 8.21 (d, J=9 Hz, 1H), 7.92 (d, J=9 Hz, 1H), 7.82 (s, 1H), 7.73 (d, J=9 Hz, 2H), 7.21 (t, J=9 Hz, 1H), 7.07 (d, J=9 Hz, 2H), 6.67 (d, J=9 Hz, 2H), 4.72 (m, 1H), 3.87 (s, 3H), 3.82 (s, 6H), 1.32 (d, J=3 Hz, 6H); Analytical HPLC: 88% pure; MS (ES-NEG): [M–H] 578; Anal. Calc. for $C_{29}H_{29}N_3O_8S$: C, 60.09, H, 5.04, N, 7.25. Found: C, 57.26, H, 4.82, N, 7.09.

EXAMPLE 18

7-(2,6-Dimethoxy-benzoylamino)-4-hydroxy-3-(4-methoxy-phenylazo)-napthalene-2-sulfonic Acid 7-(2,6-Dimethoxy-benzoylamino)-4-hydroxy-3-(4-methoxy-phenylazo)-napthalene-2-sulfonic acid isopropyl ester (Example 17, 35 mg, 0.06 mmol) was suspended in 2-butanone (3 m) and sodium iodide (18 mg, 0.12 mmol) was added. The reaction mixture was allowed to stir under nitrogen at 60° C. for 24 h. The solvent was removed under a stream of nitrogen, acetone was added and the suspension was filtered to provide the title compound (30 mg, 0.053 mmol, 89%) as a red solid: NMR (DMSO-$d_6$): δ 16.38 (s, 1H), 10.71 (s, 1H), 8.35 (d, J=9 Hz, 1H), 8.11 (s, 1H), 7.90 (m, 3H), 7.52 (s, 1H), 7.44 (t, J=9 Hz, 1H), 7.07 (d, J=9 Hz, 2H), 6.67 (d, J=9 Hz, 2H), 3.92 (s, 3H), 3.87 (s, 6H); Analytical HPLC: 87% pure; MS (ES-NEG): [M–H] 536; Anal. Calc. for $C_{26}H_{23}N_3O_8SNa$: C, 55.81, H, 3.96, N, 7.51. Found: C, 50.83, H, 4.07, N, 6.42.

EXAMPLE 19

7-(3,4-Dimethoxy-benzoylamino)-4-hydroxy-3-(4-methoxy-phenylazo)-napthalene-2-sulfonic Acid 7-Amino-4-hydroxy-3-(4-methoxy-phenylazo-napthalene-2-sulfonic acid isopropyl ester (Example 6, 100 mg, 0.24 mmol) was dissolved in dichloromethane (15 mL) and diisopropylethylamine (84 µL, 62 mg, 0.48 mmol). 3,4-Dimethoxybenzoyl chloride (56 mg, 0.28 mmol) was added under nitrogen and the reaction mixture was allowed to stir for 16 h. The solution was washed with water, 1N HCl, and saturated sodium bicarbonate solution. The organic layer was dried with $MgSO_4$ and concentrated. This concentrate was purified by chromatography (silica gel, eluent: 50% ethyl acetate/hexane) to provide the sulfonic acid, isopropyl ester (27 mg, 0.047 mmole, 17%). This ester (16 mg, 0.028 mmole) was suspended in 2-butanone (0.5 mL) and sodium iodide (6 mg, 0.041 mmole) was added. The resulting suspension was heated with stirring to 60° C. for 72 h. The solvent was removed under a stream of nitrogen. The remaining solid was suspended in acetone and filtered to provide the title compound (9 mg, 0.016 mmole, 67%, calculated from the isopropyl ester) as a red solid: NMR (DMSO-$d_6$): δ 16.30 (s, 1H), 10.39 (s, 1H), 8.26 (d, J=9 Hz, 1H), 8.17 (s, 1H), 7.96 (d, J=8 Hz, 1H), 7.90 (d, J=8 Hz, 2H), 7.68 (d, J=9 Hz, 1H), 7.58 (s, 1H), 7.50 (s, 1H), 7.10 (m, 3H), 3.95 (m, 9H): Analytical HPLC: 82% pure: MS (ES-NEG): [M–H] 536.

Pharmacology

The FSH antagonist activities of the compounds herein are demonstrable in three in vitro FSH antagonist assays and one in vivo assay.

FSH Receptor Radioligand Membrane Binding Assay

Membrane Source: Chinese hamster ovarian cells stably transfected with the human FSH receptor were cultured (Ultra CHO medium containing 1% fetal bovine serum and 200 µg/mL G418) in and harvested. Cells were collected by centrifugation and resulting cell pellets were frozen and stored at −70° C.

Membrane Receptor Preparation: Frozen cell pellets were weighed and resuspended in binding buffer to a final concentration of 30 mg wet weight/mL. Cell suspension for each pellet was homogenized using a Tempest homogenizer (setting=1; 5 strokes; VirTis, Gardiner, N.Y.). Cell homogenates were pooled and 35 mL aliquots were transferred to 50-mL polypropylene copolymer centrifuge tubes (Nalgene cat. #3110-0500). Tubes were spun at 12,000 rpm (SS34 rotor) for 12 min at 4° C. Resulting supernatant fractions were discarded and pellets were stored at −70° C. until use. On the day of the assay, 35 mL binding buffer was added to each tube (35 mL membrane suspension was sufficient for three 96-well plates). The membrane pellet was dispersed by trituration using a pipet. The resulting suspension was homogenized using a Tempest homogenizer (3 strokes at setting=1).

Receptor Binding Assay: Membrane homogenate (100 µl) was added to each well of a 96-well microtiter plate (Falcon

3077). All reactions were tested in triplicate. Test compound solutions (50 µl) were added to the designated wells. Total bound counts were determined by adding 50 µl binding buffer containing 4% DMSO to the designated wells. Non-specific binding was determined by adding 50 µl of hFSH solution to the designated wells. Plates were pre-incubated for 15 min at room temperature on shaking platform (setting=3). After preincubation [$^{125}$I]FSH (50 µl) was added to each well and plates were incubated for 2 h at room temperature on shaking platform (setting=3). The reaction was terminated by transfer of the membrane preparation to glass fiber filters (Blue Mat #11740; 102×256 mm; Skatron Instruments, Sterling, Va.) that had been pretreated with 1% BSA in wash buffer for at least 30 min, but not longer than 1 h using a 96-well microtiter vacuum harvester (Skatron Instruments). The membrane preparation was washed with 5 cycles of ice-cold wash buffer (200 µl/well/cycle) followed by a pulse wash of 3 cycles (100 µl/well/cycle). The total wash volume per well was 1.3 mL. The filters were dried by a 10 sec aspiration. Disks corresponding to each well of the microtiter plate were punched out of the filter mat into 12×75 mm polypropylene tubes. The radioactivity present on each of the disks was measured using a gamma counter.

An FSH dose response curve (0.001, 0.01, 0.1, 1, 10, and 100 nM) was generated for each binding assay to monitor assay to assay variability.

FSH Receptor Radioligand Membrane Binding Assay Buffers and Reagents

Binding Buffer (pH 7.2): 10 mM Trizma®-HCl (Sigma)

1 mM MgCl$_2$ 1 mM CaCl$_2$ 0.025% (w/v) Sodium azide 0.1% (w/v) Bovine serum albumin (fraction V; Sigma)

5 µg/mL Aprotinin

5 µg/mL Leupeptin

5 µg/mL Pepstatin

5 µg/mL Phenylmethylsulfonylfluoride

5 µg/mL Phosphoramidon

Binding buffer was prepared in 1 l volumes containing Trizma-HCl, MgCl$_2$, CaCl$_2$ and sodium azide, the pH was adjusted to 7.2 with NaOH, and stored at 4° C. until use. BSA was weighed out on the day of the assay and added to the amount of buffer required for the assay (usually 150 mL). The protease inhibitors were prepared as 1 mg/mL stocks (aprotinin, leupeptin, and phosphoramidon were prepared in binding buffer without BSA and protease inhibitors; pepstatin and PMSF were prepared in methanol), stored in 1 mL aliquots at −70° C., and added to the binding buffer on the day of the assay.

Wash Buffer (pH 7.2): 50 mM Trizma®-HCl (Sigma)

10 MM MgCl$_2$ 0.5 mM EDTA

Wash buffer was prepared containing Trizma-HCl, MgCl$_2$ and EDTA, the pH was adjusted to 7.2 with NaOH, and stored at 4° C.

Filter Soak Buffer (pH 7.2): Wash Buffer

1% BSA

BSA was weighed out on the day of the assay and added to 300 mL of wash buffer. The filter soak buffer was used for two assays before being discarded.

[$^{125}$I]hFSH Solution: The concentration of the [$^{125}$I]hFSH stock solution was determined by measuring the radioactivity in three 10 µl samples of the stock solution using a gamma counter. The concentration was calculated using the radioactivity measurement (cpm), counting efficiency (0.8) to convert cpm to dpm and subsequent conversion of dpm to µCi, specific activity µCi/µg FSH) of the [$^{125}$I]hFSH given on the specification sheets from NEN, and the molecular weight of FSH (29,695). A portion of the stock solution was diluted in binding buffer to a concentration of 200 pM.

FSH Solution for Determining Non-specific Binding: Purified human FSH was prepared as a 100 µM solution in binding buffer without protease inhibitors. This stock was stored as 30 µl aliquots at −70° C. The stock was diluted on the day of the assay to 4 µM in binding buffer containing 4% DMSO on the day of the assay.

Compound Solutions: Each compound to be tested was prepared as a 400 µM solution in DMSO. For additional concentrations, the 400 µM stock solution was diluted with binding buffer containing 4% DMSO.

References:

1) McPherson, G. A. 1985. Kinetic, EBDA, Ligand, Lowry: a collection of radioligand binding analysis programs. BIOSOFT, Cambridge, U. K.

2) Schneyer, A. L., Sluss, P. M., Bosukonda, D. and Reichert, L. E. "Electrophoretic Purification of Radioiodinated Follicle-Stimulating Hormone for Radioligand Receptor Assay and Radioimmunoassay." *Endocrinology*, 1986, 119, 1446–1453.

3) Reichert, L. E. and Bhalla, V. K. "Development of a Radioligand Tissue Receptor Assay for Human Follicle-Stimulating Hormone." *Endocrinology* 1974, 94, 483–491.

| Example | % Inhibition at 100 µM conc. | % Inhibition at 10 µM conc. | IC$_{50}$ (µM) |
|---------|------------------------------|-----------------------------|----------------|
| 3       | 94                           | 74                          | 6.0            |
| 9       | 98                           | 66                          | 5.0            |
| 11      | 71                           | 29                          | 8.6            |
| 12      |                              |                             | 101            |
| 14      | 60                           | 14                          | 81             |
| 16      | 76                           | 11                          | 79             |
| 18      | 8                            | 10                          | —              |
| 19      | 100                          | 19                          | 14             |

In Vitro Bio-assay of Agonists and Antagonists to the FSH Receptor

The following procedure was used as a screening assay to verify in vitro efficacy of compounds found to bind to the FSH receptor in the binding assay.

Methods: Reagents

Compound Vehicle: Stock compounds were solubilized in an appropriate vehicle preferably PBS/0.1% Bovine Serum Albumin (BSA; Sigma Chemical Co., St. Louis, Mo.). The compounds were subsequently diluted in sterile assay medium (Optimem (Gibco/BRL, Grand Island, N.Y.)/0.1% BSA) prior to use in the bio-assay.

Preparation of CHO-3D2 Cells; CHO-3D2 cells were plated into 96-well Nunc tissue culture plates at a density of 30,000 cells/well in DMEM/F12 medium (Gibco/BRL, Grand Island, N.Y.) supplemented with 5% Fetal Bovine Serum (Hyclone, Fetal Clone II), 2 mM L-glutamine and penicillin/streptomycin (100 U/mL). Cells were plated one day prior to performing the bio-assay.

Assay: On the day of assay, the wells were washed two times with 100 ul/well of pre-warmed (37 deg C.) assay medium. After aspirating the second wash, an additional 100 ul of assay medium was added to each well and the cells pre-incubated for 30–45 minutes at 37 deg C. in a humidified incubator with 5% CO2/95% air. The cells were then challenged with varying dilutions of the test substance(s) in a 50 ul total incubation volume in assay medium for 30 minutes at 37 deg C in the humidified incubator. The challenge was terminated by the addition of 50 ul of 0.2 N HCl to each well. cAMP accumulation in the medium was measured by radioimmunoassay.

Experimental Groups: In the 96-well format, the plate is organized into 12 columns each containing 8 rows of wells. The plate was split in half to test a single compound in both agonist and antagonist mode on the same plate.

For agonist mode, compounds were tested using 5 different concentrations in a dose-response paradigm using one column as a control (challenge medium alone) in agonist mode.

For antagonist mode, compounds were tested in a dose-response paradigm versus a constant level of purified human FSH (the ED20 (1.85 ng/mL); previously calculated during characterization of the bio-assay). The 96-well format allowed for the capability to test 4 columns of compound, using one of the remaining columns for negative control (challenge medium alone) and the other remaining column for ampositive control (ED20 of FSH alone).

The doses chosen to test each compound were extrapolated from the initial screening process (receptor binding data). Along with the test compounds, FSH was run in agonist mode using doses ranging from 0.1 ng/mL–1000 ng/mL as a positive control.

Cytotoxicity of the compounds were screened by treating cells with the highest concentration of each compound used in the cAMP assay for 30 minutes followed by washing of the cells 2 times with 100 ul PBS. The cells were then incubated for 5 min at 37 deg C in the presence of 50 ug/mL Fluorescein diacetate and 20 ug/mL Propidium iodide in 100 ul PBS. The cells were washed two times with 100 ul PBS followed by examination of the cells under a fluorescence microscope using a 490 nm filter. Viable cells stained green throughout, while dead cells had red fluorescent nuclei.

Analysis of Results: cAMP accumulation was expressed as fmol/mL. cAMP accumulation in agonist mode, or the ability of the compound to inhibit hFSH-induced cAMP accumulation in antagonist mode was compared to the appropriate negative and positive controls. Data were analyzed statistically by analysis of variance and significant differences between treatments and control determined by Dunnett's test. In antagonist mode, a Duncan's test was used.

Reference Compounds: Test compounds were compared to the effect of purified or recombinant human FSH. In this paradigm, hFSH induced a dose-dependent increase in cAMP accumulation, with apparent ED80=22.55 ng/mL, ED50=6.03 ng/mL and ED20=1.85 ng/mL, calculated using a four-parameter logistic equation.

| Example | $IC_{50}$ ($\mu$M) |
|---|---|
| 9 | 1.4 |
| 11 | 10.0 |
| 19 | 16.0 |

In Vitro Bioassay of Agonists and Antagonists to the FSH Receptor using Primary Cultures of Rat Granulosa The following procedure was used as a low-throughput functional screening assay to study in vitro efficacy of compounds found to be agonists or antagonists of the FSH receptor.

Materials and Methods: Reagents

Compound Vehicle: Stock compounds were solubilized in an appropriate vehicle, preferably PBS (phosphate buffered saline) or DMSO (dimethyl sulfoxide), at a concentration of 0.1 M. The compounds were subsequently diluted in sterile challenge medium [McCoy's 5A medium (Gibco/BRL, Grand Island, N.Y.) supplemented with 5 mg/mL insulin, 5 mg/mL transferrin, 5 ng/mL sodium selenite (ITS, Sigma Chemical Co., St. Louis, Mo.), 146 mg/mL L-glutamine, 100 nM testosterone, 100 nM DES and 100 U/mL penicillin/ 10 mg/mL streptomycin/250 ng/mL amphotericin B (antibiotic/antimycotic, Gibco) and 0.1% bovine serum albumin (Sigma, St. Louis, Mo.)] prior to use in the assay. The concentration of vehicle was maintained constant throughout all dilutions.

Preparation of Granulosa Cells: Twenty-four day-old immature female Sprague-Dawley rats (Charles River Laboratories, Wilmington, Mass.) were used as donors for ovarian granulosa cells. The animals were treated by single daily injections of 100 mg/kg diethylstilbestrol (DES) in oil over three days. On the fourth day, animals were sacrificed by $CO_2$ asphyxiation and the ovaries were removed. Ovaries were washed three times in 50 mL of sterile HEPES-buffered saline (HBS, pH 7.4). Granulosa cells were harvested by incubating ovaries in a hypertonic medium consisting of serum-free McCoy*s 5A medium (Gibco Life Sciences, Grand Island, N.Y.) supplemented with 5 mg/mL insulin, 5 mg/mL transferrin, 5 ng/mL sodium selenite (ITS, Sigma Chemical Co., St. Louis Mo.), 146 mg/mL L-glutamine, 100 nM testosterone, 100 nM DES and 100 U/mL penicillin/10 mg/mL streptomycin/250 ng/mL amphotericin B (antibiotic/antimycotic, Gibco) containing 0.5 M sucrose and 0.1 mM EGTA. Ovaries were then incubated for 45 min. at 37 C in a humidified incubator gassed with 95% air/5% $CO_2$. They were washed 3 times with 10 mL isotonic medium (hypertonic medium without sucrose and EGTA) and incubated another 45 min. in isotonic medium at 37 C. Granulosa cells were harvested by squeezing the ovaries between two sterile glass microscope slides. Isolated granulosa cells were then placed in an 50 mL centrifuge tube and washed two times by the addition of 50 mL serum-free McCoy*s 5A medium followed by centrifugation at 700×g for 5 min. After the final spin, the cells were resuspended by gentle trituration in 25 mL serum-free medium, an aliquot counted in a hemocytometer and viability estimated by trypan blue exclusion. Cells were plated into 24-well Nunc tissue culture plates at 200,000 viable cells/well in 250 mL.

Assay: Following plating of the cells, the plates are incubated at 37 C for 2–4 hours at which time the treatments are added to the cells. Treatments are added to the wells at 2X the desired final concentration in 250 mL/well in isotonic medium containing 0.2% BSA. The cells are incubated at 37 C for 72 h. At the end of the incubation period, the medium is removed from the wells and assayed for estradiol concentration by radioimmunoassay.

Experimental Groups: In the 24-well format, the plate was divided into 6 columns of 4 wells/column. One plate per compound was used to test either agonist or antagonist modes.

In agonist mode, each compound was tested in a dose-response paradigm using 5 different doses of the compound and compared the activity to the 6th column of cells which received vehicle alone.

For antagonist mode, each compound was tested in a dose-response paradigm versus a constant level of purified human FSH (the ED50 0.5 ng/mL; previously calculated during the characterization of the bioassay). Four different doses of compound were tested in the antagonist mode. In addition, one column was used for a negative control (vehicle alone) and the other remaining column for a positive control (ED50 of FSH alone).

The doses of compound chosen to test were extrapolated from the initial functional screening process. Along with the plates testing compounds, another plate was run in parallel using a dose-response of FSH (0.01–100 ng/mL) as a positive control.

Analysis of Results: Estradiol was expressed as pg/mL. Estradiol secretion in agonist mode, or the ability of the compound to inhibit FSH-induced estradiol secretion in antagonist, was compared to the appropriate negative and positive controls. Data were analyzed statistically by analysis of variance with Huber weighting of log transformed data. Paired differences were determined using the LSD test Reference Compounds: Test compounds were compared to the effect of purified or recombinant human FSH.

Activity: Compounds which significantly increase estradiol secretion as compared to the negative control in agonist mode or significantly inhibited FSH-induced estradiol secretion in antagonist mode were considered active. EC50: Concentration of the compound that gave half-maximal response in terms of estradiol secretion over negative control (agonist mode only). IC50: Concentration of compound that gave half-maximal inhibition of FSH-induced estradiol secretion (for antagonist mode only).

References:
Hsueh, A. J., Bicsak, T., Jia, X. -C., Dahl, K. D., Fauser, B. C. J. M., Galway, A. B., Czwkala, N., Pavlou, S., Pakoff, H., Keene, J., Boime, I, "Granulosa Cells as Hormone Targets: The role of Biologically Active Follicle-Stimulating Hormone in Reproduction" Rec. Prog. Horm. Res., 1989, 45, 209–277

| Example | $IC_{50}$ ($\mu$M) |
|---------|---------|
| 9 | 1.9 |

What is claimed:
1. A compound of the formula (I):

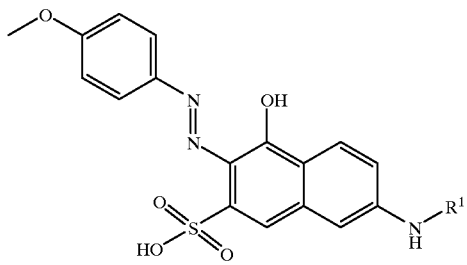

(I)

wherein:
$R^1$ is a moiety selected from:

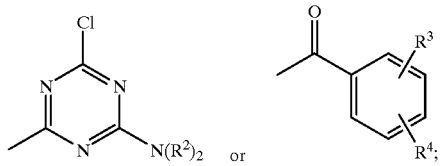

$R^2$ is $CH_2CH_2CONH_2$ or $CH_2CH_2OH$;
$R^3$ and $R^4$ are independent substituents selected from the group consisting of H, or —$OCH_3$;
or a pharmaceutically acceptable salt or ester form thereof.

2. A compound of claim 1 which is 7-{4-[bis-(2-carbamoyl-ethyl)-amino]-6-chloro-[1,3,5]-triazin-2-ylamino)-4-hydroxy-3-(4-methoxy-phenylazo)-napthalene-2-sulfonic acid, or a pharmaceutically acceptable salt or ester form thereof.

3. A compound which is 7-(H-fluorene-9-ylmethoxycarbonylamino)-4-hydroxy-3-(4-methoxy-phenylazo)-napthalene-2-sulfonic acid.

4. A compound which is 7-(H-fluorene-9-ylmethoxycarbonylamino)-4-hydroxy-3-(4-methoxy-phenylazo)-napthalene-2-sulfonic acid isopropyl ester.

5. A compound which is 7-amino-4-hydroxy-3-(4-methoxy-phenylazo)-napthalene-2-sulfonic acid isopropyl ester.

6. A compound which is 7-(4,6-dichloro-[1,3,5]-triazin-2-ylamino)-4-hydroxy-3-(4-methoxy-phenylazo)-napthalene-2-sulfonic acid isopropyl ester.

7. A compound which is 7-{4-[bis-(2-carbamoyl-ethyl)-amino]-6-chloro-[1,3,5]-triazin-2-ylamino)-4-hydroxy-3-(4-methoxy-phenylazo)-napthalene-2-sulfonic acid isopropyl ester.

8. A compound which is 7-{4-[bis-(2-hydroxy-ethyl)-amino]-6-chloro-[1,3,5]-triazin-2-ylamino)-4-hydroxy-3-(4-methoxy-phenylazo)-napthalene-2-sulfonic acid isopropyl ester.

9. A compound of claim 1 which is 7-{4-[bis-(2-hydroxy-ethyl)-amino]-6-chloro-[1,3,5]-triazin-2-ylamino)-4-hydroxy-3-(4-methoxy-phenylazo)-napthalene-2-sulfonic acid, or a pharmaceutically acceptable salt or ester form thereof.

10. A compound which is 7-(3,5-dimethoxy-benzoylamino)-4-hydroxy-3-(4-methoxy-phenylazo)-napthalene-2-sulfonic acid isopropyl ester.

11. A compound of claim 1 which is 7-(3,5-dimethoxy-benzoylamino)-4-hydroxy-3-(4-methoxy-phenylazo)-napthalene-2-sulfonic acid, or a pharmaceutically acceptable salt or ester form thereof.

12. A compound which is 7-benzoylamino-4-hydroxy-3-(4-methoxy-phenylazo)-napthalene-2-sulfonic acid isopropyl ester.

13. A compound of claim 1 which is 7-benzoylamino-4-hydroxy-3-(4-methoxy-phenylazo)-napthalene-2-sulfonic acid or a pharmaceutically acceptable salt or ester form thereof.

14. A compound which is 7-(2,6-dimethoxy-benzoylamino)-4-hydroxy-3-(4-methoxy-phenylazo)-napthalene-2-sulfonic acid isopropyl ester.

15. A compound of claim 1 which is 7-(2,6-dimethoxy-benzoylamino)-4-hydroxy-3-(4-methoxy-phenylazo)-napthalene-2-sulfonic acid, or a pharmaceutically acceptable salt or ester form thereof.

16. A compound of claim 1 which is 7-(3,4-dimethoxy-benzoylamino)-4-hydroxy-3-(4-methoxy-phenylazo)-napthalene-2-sulfonic acid, or a pharmaceutically acceptable salt or ester form thereof.

17. A method of inducing contraception in a mammal, the method comprising administering to a mammal in need thereof a pharmaceutically effective amount of a compound of claim 1, or a pharmaceutically acceptable salt or ester form thereof.

18. A pharmaceutical composition comprising a pharmaceutically effective amount of a compound of claim 1, or a pharmaceutically acceptable salt or ester form thereof, and a pharmaceutically acceptable carrier or excipient.

* * * * *